United States Patent
Cosoleto et al.

(10) Patent No.: US 11,740,222 B2
(45) Date of Patent: Aug. 29, 2023

(54) MAGNETIC HEAD FOR A MAGNETIC DETECTOR FOR DETECTING METAL PARTICLES, AND MAGNETIC DETECTOR PROVIDED WITH SUCH A HEAD

(71) Applicant: SAFRAN AEROSYSTEMS FLUID, Soignolles en Brie (FR)

(72) Inventors: David Cosoleto, Moissy-Cramayel (FR); Patrick Bourbon, Moissy-Cramayel (FR); Denis Sindezingue, Moissy-Cramayel (FR)

(73) Assignee: SAFRAN AEROSYSTEMS FLUID, Soignolles en Brie (FR)

( * ) Notice: Subject to any disclaimer, the term of this patent is extended or adjusted under 35 U.S.C. 154(b) by 59 days.

(21) Appl. No.: 17/425,405

(22) PCT Filed: Jan. 21, 2020

(86) PCT No.: PCT/EP2020/051425
§ 371 (c)(1),
(2) Date: Jan. 12, 2022

(87) PCT Pub. No.: WO2020/152175
PCT Pub. Date: Jul. 30, 2020

(65) Prior Publication Data
US 2022/0390429 A1 Dec. 8, 2022

(30) Foreign Application Priority Data
Jan. 25, 2019 (FR) ...................................... 1900682

(51) Int. Cl.
*G01N 33/28* (2006.01)
*F01M 11/10* (2006.01)
(Continued)

(52) U.S. Cl.
CPC ......... *G01N 33/2858* (2013.01); *F01M 11/10* (2013.01); *F01M 2001/1042* (2013.01);
(Continued)

(58) Field of Classification Search
None
See application file for complete search history.

(56) References Cited

U.S. PATENT DOCUMENTS 3,457,504 A * 7/1969 Arthur ............... G01N 15/0656
324/609
4,823,625 A * 4/1989 Hamilton ................. G07C 3/00
324/717

(Continued)

FOREIGN PATENT DOCUMENTS

CA 2818374 A1 * 9/2014 ........... E21B 47/102
CN 106796130 A * 5/2017 ............... B08B 3/12
(Continued)

OTHER PUBLICATIONS

International Search Report dated Mar. 19, 2020, issued in corresponding International Application No. PCT/EP2020/051425, filed on Jan. 21, 2020, and its English translation thereof, 5 pages.
(Continued)

*Primary Examiner* — Kevin R Steckbauer
(74) *Attorney, Agent, or Firm* — Christensen O'Connor Johnson Kindness PLLC

(57) ABSTRACT

A magnetic head for a magnetic detector for detecting metal particles in a hydraulic circuit includes an axial body internally including at least one magnet, at least a first electrode defining an air gap zone located in the magnetic field created by the magnet, such that the circuit creates a particle alignment zone in the air gap, and an electrical connector for electrically connecting the electrodes. The magnet can be a diametrically magnetized magnet.

14 Claims, 15 Drawing Sheets

(51) Int. Cl.
*F01M 1/10* (2006.01)
*F16N 29/00* (2006.01)

(52) U.S. Cl.
CPC ........ *F01M 2011/144* (2013.01); *F16N 29/00* (2013.01); *F16N 2200/04* (2013.01)

(56) References Cited

U.S. PATENT DOCUMENTS

| | | | |
|---|---|---|---|
| 5,027,065 A | 6/1991 | Bares et al. | |
| 5,064,530 A * | 11/1991 | Duff | G01N 33/2888 210/512.3 |
| 5,179,346 A * | 1/1993 | McGee | G01N 15/0656 324/693 |
| 5,384,535 A | 1/1995 | Mayeur | |
| 5,402,113 A * | 3/1995 | Naas | G01N 33/2858 324/698 |
| 5,604,441 A * | 2/1997 | Freese, V | G01N 33/2888 324/663 |
| 5,696,331 A * | 12/1997 | Otsuka | G01N 15/0656 73/865.8 |
| 7,845,238 B2 * | 12/2010 | Ruchel | G01F 1/58 73/861.12 |
| 10,458,970 B2 * | 10/2019 | Kim | G01N 33/1813 |
| 10,705,039 B2 * | 7/2020 | Kiriyama | G01N 33/2858 |
| 10,746,577 B2 * | 8/2020 | Shi | G01F 1/584 |
| 10,837,884 B2 * | 11/2020 | Mou | G01N 33/0014 |
| 10,969,310 B2 * | 4/2021 | Mou | G01N 15/06 |
| 11,435,029 B2 * | 9/2022 | Basso | G01N 15/0656 |
| 2009/0038409 A1 * | 2/2009 | Ruchel | G01F 1/58 73/861.12 |
| 2014/0294625 A1 * | 10/2014 | Tucker | B60G 17/0195 310/68 B |
| 2014/0347032 A1 | 11/2014 | Reed et al. | |
| 2015/0061650 A1 * | 3/2015 | Strietzel | G01D 5/204 324/207.15 |
| 2015/0377666 A1 * | 12/2015 | Rovner | G01F 15/18 73/861.12 |
| 2017/0115146 A1 * | 4/2017 | Shi | G01F 25/10 |
| 2017/0307580 A1 * | 10/2017 | Kim | G01N 27/08 |
| 2018/0275083 A1 * | 9/2018 | Kiriyama | G01N 33/2858 |
| 2019/0085875 A1 * | 3/2019 | Slama | G01D 5/12 |
| 2019/0331564 A1 * | 10/2019 | Mou | G01N 33/0014 |
| 2019/0331565 A1 * | 10/2019 | Mou | G01N 15/06 |
| 2020/0088350 A1 * | 3/2020 | Basso | B03C 1/286 |
| 2021/0181177 A1 * | 6/2021 | Sakurai | G01N 15/0606 |
| 2022/0390429 A1 * | 12/2022 | Cosoleto | F16N 29/00 |

FOREIGN PATENT DOCUMENTS

| | | | | |
|---|---|---|---|---|
| CN | 108663415 A | * | 10/2018 | ........ G01N 15/0606 |
| CN | 112986337 A | * | 6/2021 | ........ G01N 15/0606 |
| CN | 113439175 A | * | 9/2021 | ............ F01M 11/10 |
| CN | 113495044 A | * | 10/2021 | |
| CN | 113495044 B | * | 5/2022 | |
| DE | 102017204304 A1 | * | 9/2018 | ........ G01N 15/0656 |
| DE | 102018204674 A1 | * | 9/2018 | ........ G01N 15/0606 |
| EP | 0398800 A1 | | 11/1990 | |
| EP | 3561479 A1 | * | 10/2019 | .......... B01D 53/005 |
| EP | 3561481 A1 | * | 10/2019 | .......... B01D 53/005 |
| EP | 3627032 A1 | * | 3/2020 | .............. B03C 1/28 |
| EP | 3839504 A2 | * | 6/2021 | ........ G01N 15/0606 |
| EP | 3888792 A1 | * | 10/2021 | ........... B03C 1/0332 |
| EP | 3914847 A1 | * | 12/2021 | ............ F01M 11/10 |
| EP | 3627032 B1 | * | 11/2022 | .............. B03C 1/28 |
| EP | 3914847 B1 | * | 11/2022 | ............ F01M 11/10 |
| FR | 2686693 A1 | | 7/1993 | |
| FR | 3092010 A1 | * | 7/2020 | ............ F01M 11/10 |
| FR | 3092010 B1 | * | 1/2021 | ............ F01M 11/10 |
| JP | H0564751 U | | 8/1993 | |
| JP | 2016085094 A | * | 5/2016 | ............. F01N 11/00 |
| JP | 2017129552 A | * | 7/2017 | ............. F01N 11/00 |
| JP | 2018163133 A | * | 10/2018 | ........ G01N 15/0606 |
| JP | 2020183932 A | * | 11/2020 | ........ G01N 15/0606 |
| JP | 2021096168 A | * | 6/2021 | ........ G01N 15/0606 |
| JP | 7094081 B2 | * | 7/2022 | ........ G01N 15/0606 |
| TW | 202127021 A | * | 7/2021 | ........ G01N 15/0606 |
| WO | WO-2007141194 A1 | * | 12/2007 | ............... B05D 7/22 |
| WO | WO-2007141195 A1 | * | 12/2007 | ............... B05D 7/22 |
| WO | WO-2009019105 A1 | * | 2/2009 | ............. G01F 1/58 |
| WO | WO-2016027894 A1 | * | 2/2016 | ........ G01N 15/0656 |
| WO | WO-2016063491 A1 | * | 4/2016 | ............. F01N 11/00 |
| WO | WO-2020152175 A1 | * | 7/2020 | ............ F01M 11/10 |
| WO | WO-2021104892 A1 | * | 6/2021 | ........... B03C 1/0332 |

OTHER PUBLICATIONS

Written Opinion of the International Searching Authority dated Mar. 19, 2020, issued in corresponding International Application No. PCT/EP2020/051425, filed on Jan. 21, 2020, 5 pages.

* cited by examiner

[Fig 1]
(PRIOR ART)
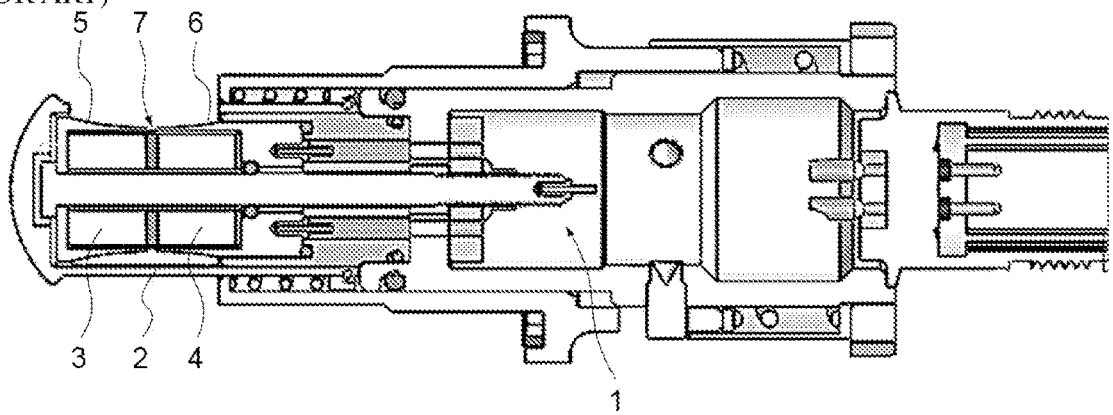
[Fig 2]
(PRIOR ART)
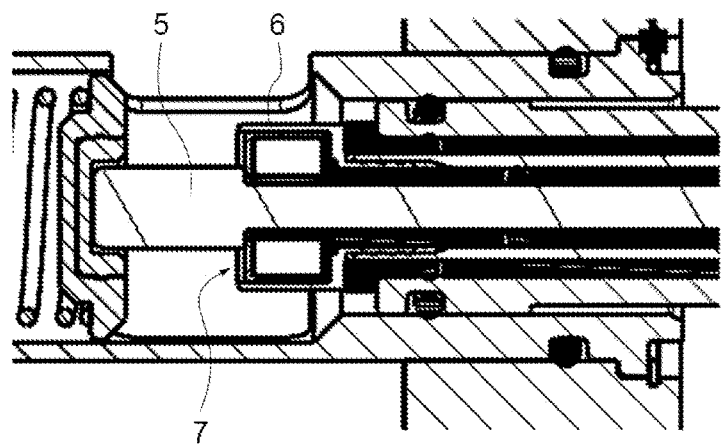

[Fig. 3]
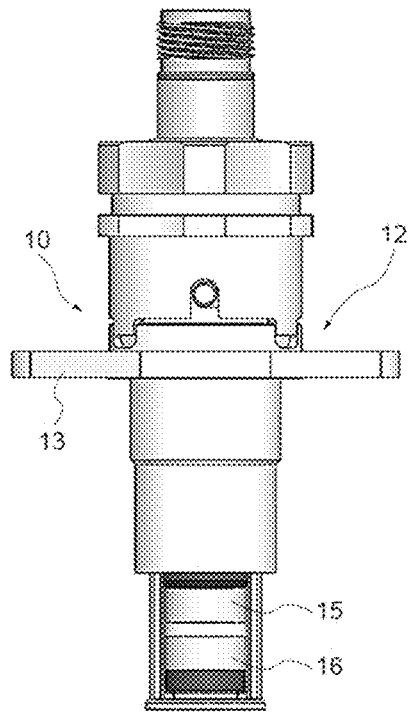
[Fig. 4]
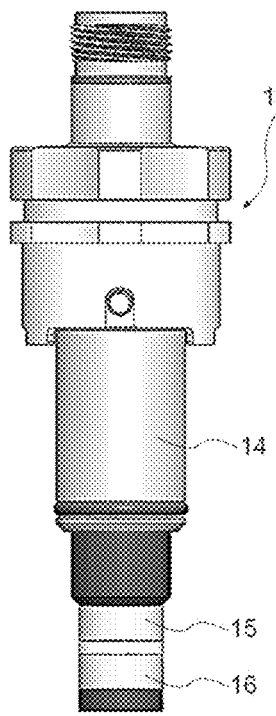

[Fig. 5]
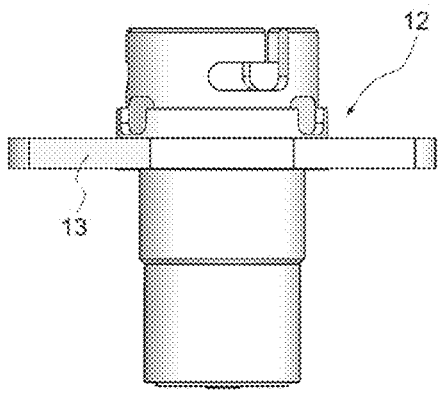
[Fig. 6]
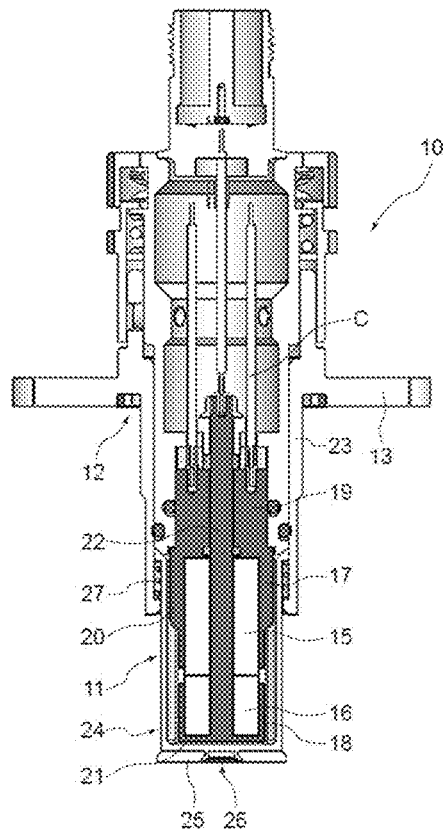

[Fig. 7]
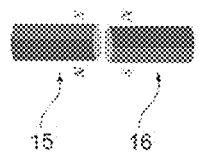
15  16
[Fig. 8]
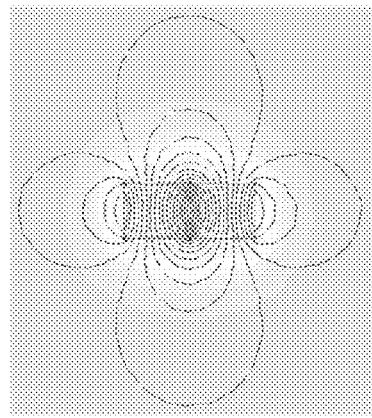
[Fig. 9]
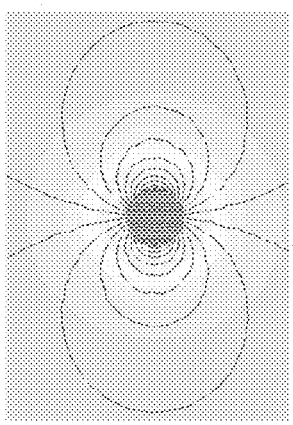

[Fig. 10]
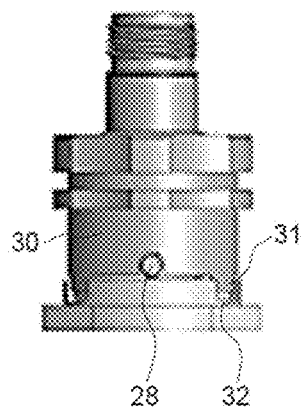
[Fig. 11]
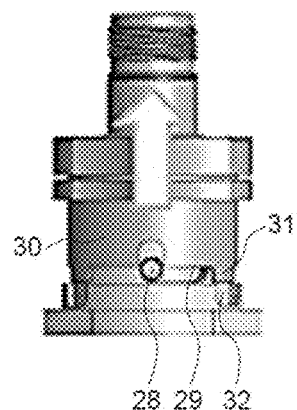
[Fig. 12]
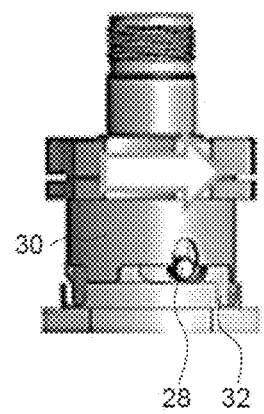

[Fig. 13]
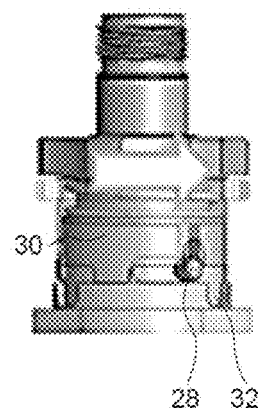
[Fig. 14]
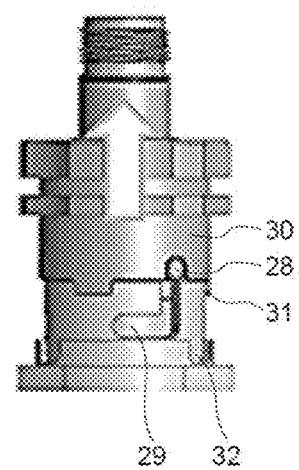
[Fig. 15]
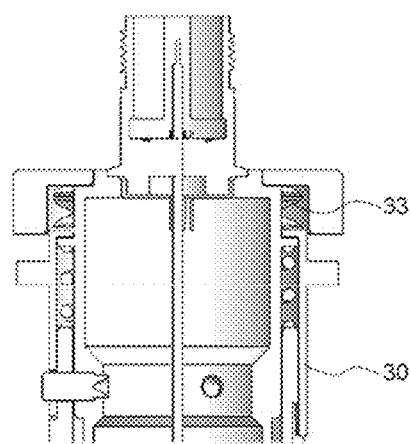

[Fig. 16a]
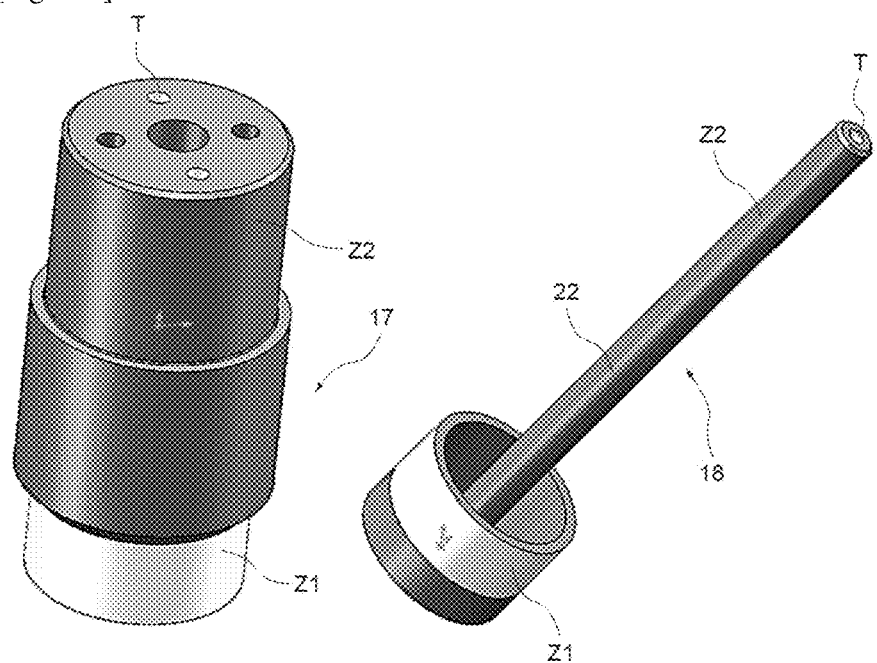
[Fig. 16b]
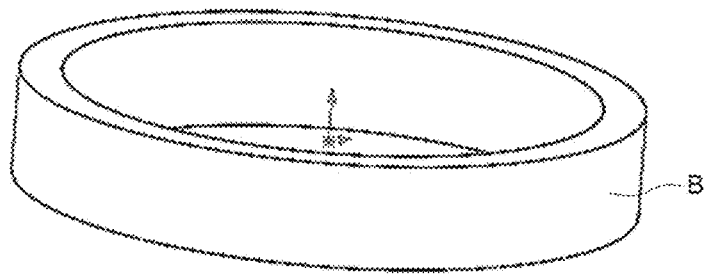

[Fig. 17]
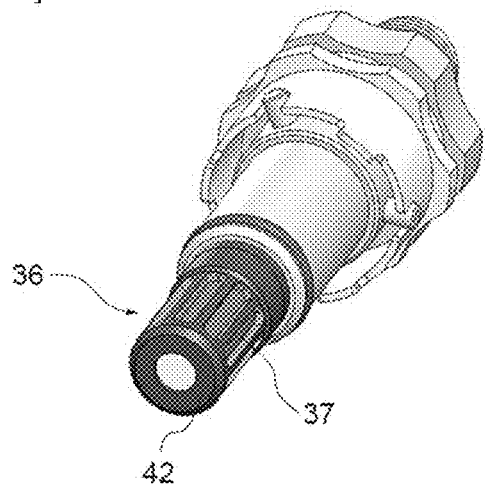
[Fig. 18]
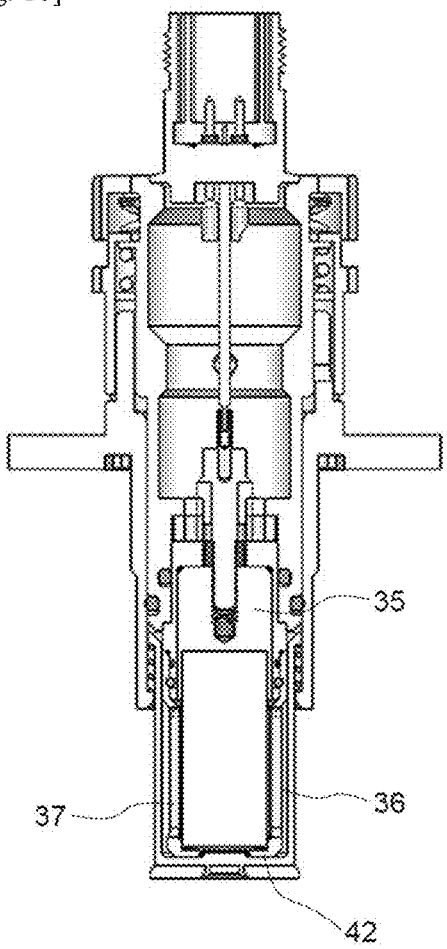

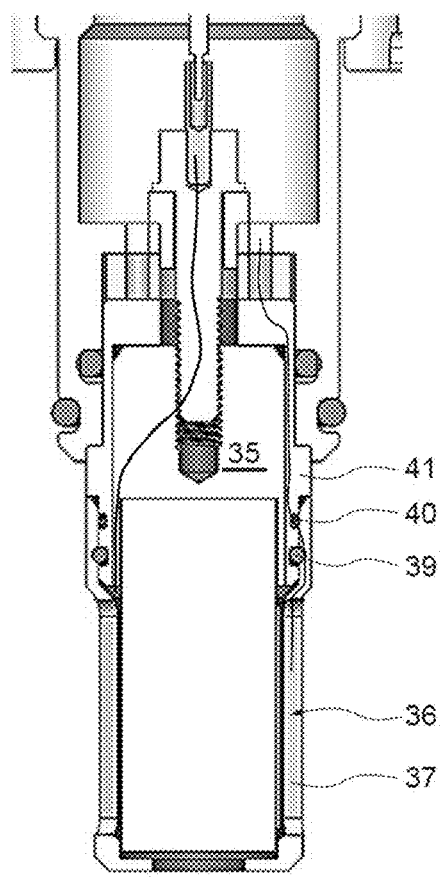
[Fig. 19]

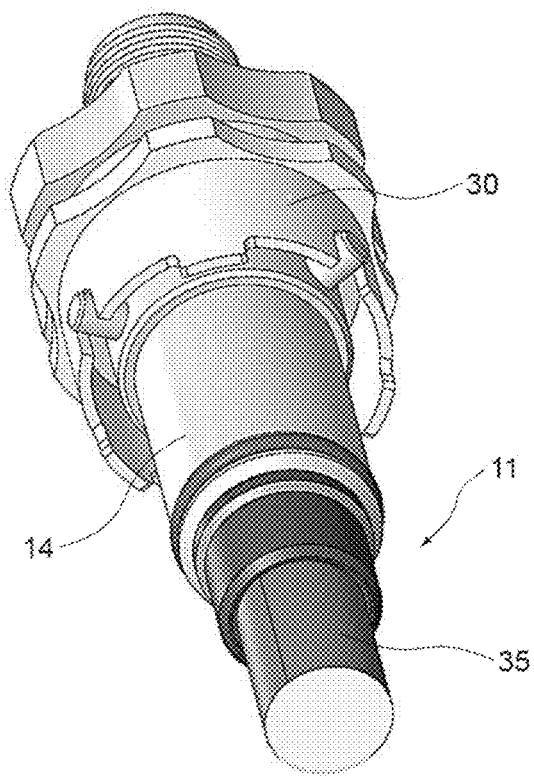
[Fig. 20]

[Fig. 21]
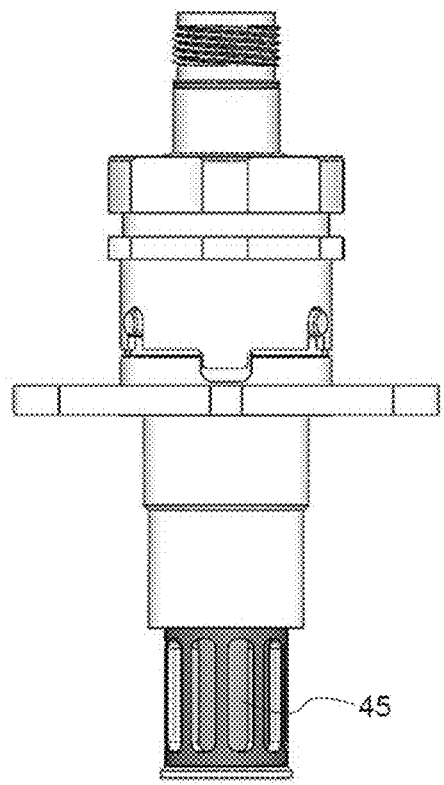
[Fig. 22]
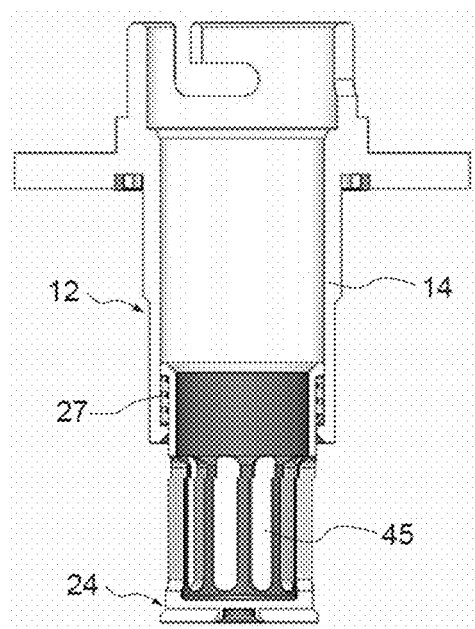

[Fig. 23]
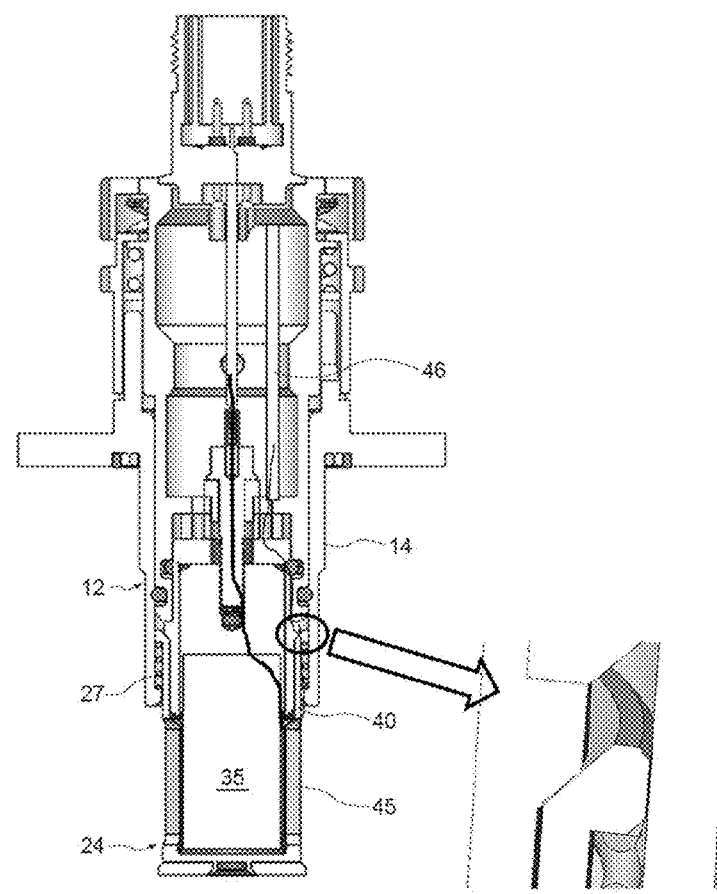
[Fig. 24]
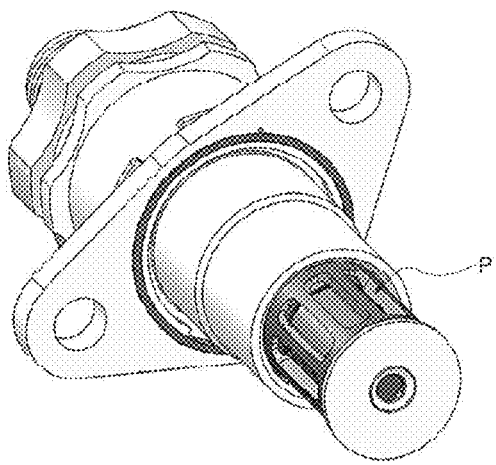

[Fig. 25]
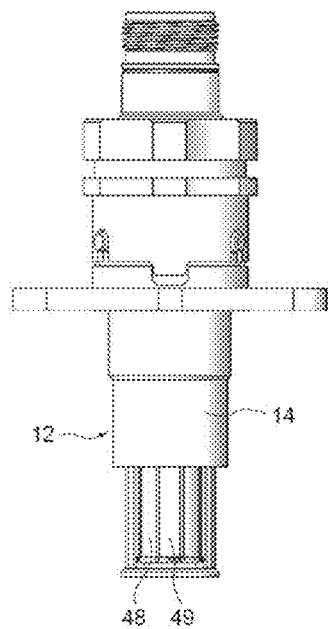
[Fig. 26]
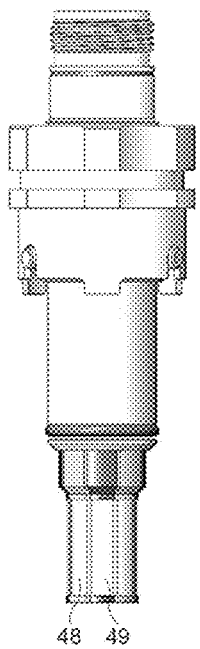

[Fig. 27]
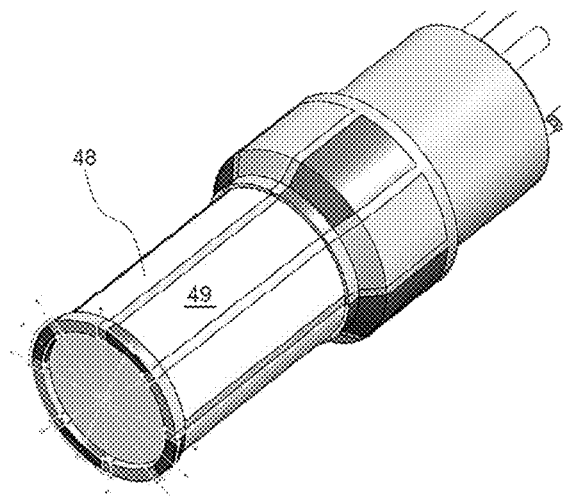
[Fig. 28]
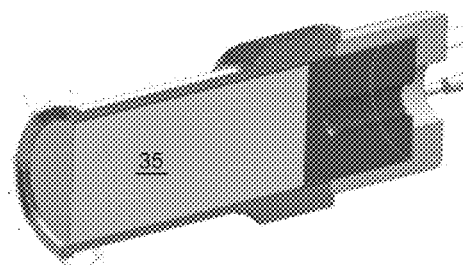
[Fig. 29]
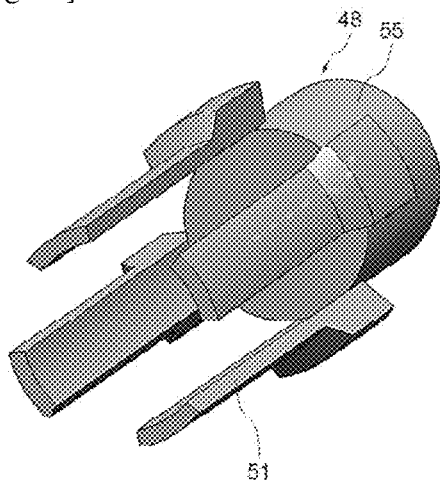

[Fig. 30]
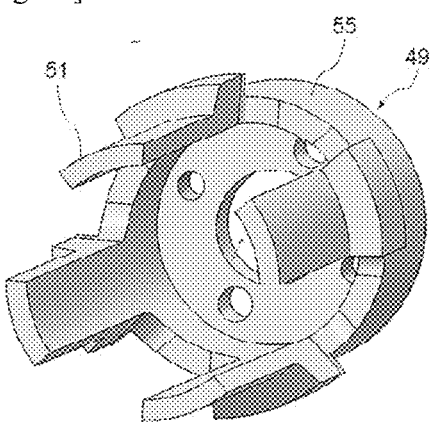
[Fig. 31]
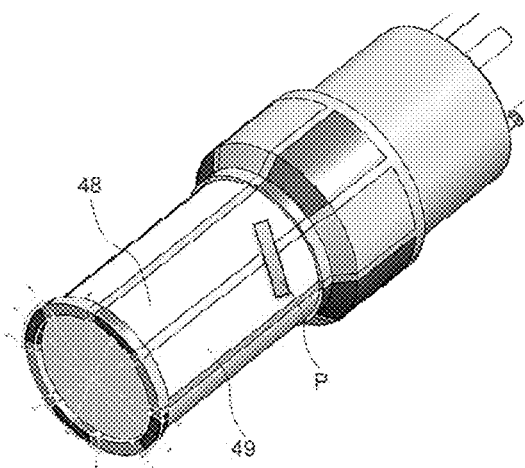

MAGNETIC HEAD FOR A MAGNETIC DETECTOR FOR DETECTING METAL PARTICLES, AND MAGNETIC DETECTOR PROVIDED WITH SUCH A HEAD

CROSS-REFERENCES TO RELATED APPLICATIONS

This application is a National Stage of International Application No. PCT/EP2020/051425 filed Jan. 1, 2020, which claims priority to French Patent Application No. 1900682, filed Jan. 1, 2019, the entire disclosures of which are hereby incorporated by reference.

The present invention relates to magnetic detectors for detecting metal particles that may be present in a hydraulic circuit.

In particular, the invention relates to the magnetic detection of metal particles in motors or in gear boxes.

The invention relates more particularly to a magnetic head intended to be installed in a magnetic detector, as well as a magnetic detector provided with such a magnetic head.

In a particularly attractive application of the invention, the magnetic detector is intended to be used to detect metal particles in a hydraulic circuit of an aircraft so as to detect, by analysis, any possible wear of mechanical parts.

Magnetic detectors of the prior art use a magnetic head that comprises, on the one hand, one or more magnets, at least two electrodes made of electrically conductive material that are insulated from each other and placed in the vicinity of the magnet such that the air gap is located in the magnetization zone of the magnet, and, on the other hand, insulators that provide for electrical insulation of the electrodes.

The insulators are commonly tubular and are placed around the magnets. The electrodes are electrically connected to the computer of the aircraft.

If metal particles are present, they are drawn to the magnets. When a sufficient quantity of particles is found in the air gap zone, the electrical resistance between the electrodes decreases. This drop in electrical resistance is detected by the computer of the aircraft and is indicated to the pilot of the aircraft.

FIG. 1 shows an embodiment example of a conventional magnetic detector of metal particles.

This detector, which is intended to be installed, for example, in an oil sump, comprises a magnetic head 1 which is installed in a receptacle 2 and which comprises two magnets 3 and 4 surrounded by respective tubular electrodes 5 and 6 separated by an air gap 7.

In the embodiment of FIG. 1, the air gap 7 is an axial air gap.

As shown in FIG. 2, there are also known magnetic detectors in which the head is provided with a radial air gap.

Indeed, here one can see that the magnetic head comprises an annular magnet. One of the electrodes 5 is an axial electrode, the other electrode 6 being placed around the magnet. In this way the air gap extends radially with respect to the general axis of the magnetic head.

It has been found that the overall effectiveness of magnetic particle detectors, commonly referred to as "Electrical Chip detectors" (ECDs), is quite poor.

This low effectiveness is due to a certain number of parameters that impact the capture and detection of metal particles.

In particular, involved are areas of turbulent flow, oil flow flowing outside the magnetic range of the detectors, etc., or, generally speaking, properties of the lubrication system.

The low rate of metal particle gathering is generally due to the specific properties of the magnet and the general volume of the magnetic head, which limit the particle capture zone.

The purpose of the invention is therefore to overcome all or a portion of the drawbacks associated with the use of magnetic heads according to the prior art, and in particular to increase the power of the magnetic field created by the magnet so as to increase the amount of captured particles and the concentration of the particles in the air gap.

Consequently, an initial aspect proposes a magnetic head for a magnetic detector for detecting metal particles in a hydraulic circuit comprising an axial body internally comprising at least one magnet, at least a first electrode defining an air gap zone located in the magnetic field created by the magnet, such that the magnet creates a particle alignment zone in the air gap, and means for electrically connecting the electrodes.

The magnet is a diametrically magnetized magnet.

This diametrical magnetization makes it possible to position the zones with the strongest magnetic field, i.e. the poles, in the fluid area containing particles to be captured, and thereby to obtain a higher rate of captured particles.

In one embodiment, the magnetic head comprises at least two diametrically magnetized magnets arranged axially, one as an extension of the other and spaced apart from each other, so that the pole of one of the magnets is located in front of an opposite pole of the other magnet, and at least two electrodes arranged around the magnets, respectively.

In various embodiments, at least one of the electrodes is secured to the body by threaded fastener.

In another embodiment, the electrode surrounds the magnet and includes a set of openings, each of which comprising two electrically conductive zones opposite each other, and each defining an air gap.

The magnet can be electrically conductive and constitute one of the electrodes of the magnetic head.

In another embodiment, each of the electrodes comprises a set of teeth extending axially from a base, the electrodes being placed coaxially one inside the other and around the magnet in such a way that the teeth of one of the electrodes are placed between the teeth of the other electrode with an insulator placed in between.

In various embodiments, each of the electrodes can be made of an electrically conductive material coated with an insulating material, and may comprise electrically conductive zones without insulation in the location of the air gap zone, and means for electrically connecting the electrodes.

The insulation is provided, for example, by overmoulding with an insulating material.

In various embodiments, the magnetic head includes advantageously includes means for attaching the magnetic head to a receptacle and means for locking the attachment means.

For example, the attachment means comprise twist-lock attachment means, the locking means comprising a lock ring capable of preventing a rotation of the twist-lock attachment means.

Advantageously, the magnet is a permanent magnet made of Neodymium Iron Boron (NdFeB).

The subject matter of the invention is also a magnetic detector of metal particles in a hydraulic circuit, comprising a magnetic head as defined above and a receptacle in which the magnetic head is placed.

In one embodiment, the receptacle comprises an end cap in which the magnet is housed.

For example, the end cap of the receptacle constitutes one of the electrodes of the magnetic detector and includes a set of openings, each of which defining an air gap, each opening including two electrically conductive zones that are opposite each other.

Advantageously, the end cap includes a flap drawn to the closed state and which can be actuated to open by the action of the magnetic head.

BRIEF DESCRIPTION OF THE DRAWINGS

Other purposes, features, and advantages of the invention will become clear from a reading of the following description, given solely as an example and in reference to the appended drawings, in which:

FIG. 1 and FIG. 2 which have already been mentioned, show two embodiments of a magnetic detector according to the prior art, one with an axial air gap and the other with a radial air gap, respectively;

FIG. 3 shows a first embodiment of a magnetic detector according to the invention;

FIG. 4 and FIG. 5 show a magnetic head and a receptacle of the detector in FIG. 3, respectively;

FIG. 6 is a cross-sectional view of the magnetic detector of FIG. 3;

FIG. 7 shows an embodiment example of a diametrically magnetized magnet of the magnetic detector in FIG. 3;

FIG. 8 and FIG. 9 show a side view and a cross-sectional view, respectively, of the magnet in FIG. 7, showing the magnetic field lines;

FIG. 10, FIG. 11, FIG. 12, FIG. 13, and FIG. 14 show the means of attachment of the magnetic head to the receptacle and the means for locking the attachment means;

FIG. 15 shows a detail of the locking means;

FIG. 16a shows an embodiment example of the electrodes;

FIG. 16b shows an embodiment example of insulation between electrodes;

FIG. 17 shows another embodiment of a magnetic head according to a second embodiment;

FIG. 18 is a cross-sectional view of the magnetic head in FIG. 17;

FIG. 19 is a larger-scale cross-sectional view of the magnetic detector in FIG. 17, showing the paths of electrical continuity;

FIG. 20 shows another embodiment of a magnetic head according to the invention;

FIG. 21 is a side view of a magnetic detector equipped with a magnetic head according to FIG. 20;

FIG. 22 is a cross-sectional view of the receptacle of the magnetic detector in FIG. 21;

FIG. 23 is a cross-sectional view of the detector in FIG. 21 showing the paths of electrical continuity in the magnetic head and in the receptacle;

FIG. 24 is a perspective view of the magnetic detector in FIG. 21 in the presence of a metal particle;

FIG. 25 is a side view of a magnetic detector according to yet another embodiment;

FIG. 26 shows the magnetic head of the detector in FIG. 25;

FIG. 27 is a detail view of the end of the magnetic head in FIG. 26, showing the structure of the magnet and the electrodes;

FIG. 28 is an axial cross-sectional view of the magnetic head in FIG. 27;

FIG. 29, and FIG. 30 show the structure of the electrodes of the magnetic head in FIG. 27; and

FIG. 31 shows the end of the magnetic head in FIG. 27 in the presence of a metal particle P.

We refer first to FIGS. 3 to 15 and 16a and 16b, which show a first embodiment of a magnetic detector of metal particles and a corresponding magnetic head according to a first embodiment.

In the embodiment contemplated here, the magnetic detector is intended to be installed in an oil sump of a motorized system of an aircraft. However, the invention is not limited to this application and indeed generally includes the detection of metal particles in a liquid in a hydraulic circuit.

Referring first to FIGS. 3 to 5, the magnetic detector, designated by the general reference number 10, essentially comprises a magnetic head 11 which is installed in a receptacle 12. As illustrated, the assembly is installed on the sump by means of a flange 13 provided on the receptacle, which cooperates with a screw-and-nut system provided on the sump. Naturally, other means of attachment, such as, for example, with studs, can also be used as a variant. The magnetic detector can also be installed on the sump by means of threads provided directly on the outer peripheral surface of the receptacle.

The magnetic head 11 comprises an axial body 14 having a generally cylindrical shape, in which is installed one or more diametrically magnetized magnets 15 and 16 and one or more corresponding electrodes 17 and 18. In the embodiment shown in FIGS. 1 to 15 and 16a and 16b, the magnetic head includes a proximal electrode 17 which essentially extends into the body 14, and a distal electrode 18.

In reference to FIGS. 7 to 9, the magnetic head comprises two diametrically magnetized cylindrical magnets placed end-to-end, one as the extension of the other, and spaced axially apart in such a way that the N pole of one of the magnets is located in front of the opposite S pole of the other magnet.

This arrangement of the diametrically magnetized magnets makes it possible to create a magnetic field in the air gap between the two magnets having field lines that tend to align the particles, which is favourable for improving detection. The diametrical orientation of the magnetization makes it possible to optimize capture, and the oppositional placement of the two magnets improves detection of the particles in the air gap between the two magnets.

In reality, the magnets have an annular transverse cross-ssection and are kept between the electrodes 17 and 18. The first proximal electrode 17 includes a base 19 secured by threaded fastener to the body of the magnetic head and a cylindrical skirt 20 surrounding the first magnet 15.

The second distal electrode 18 also comprises a base 21 and a cylindrical extension extending from the base. It includes an axial rod 22 for the attachment thereof by threaded fastener to the body of the magnetic head.

The proximal end of each electrode is provided with electrical connection means for connecting to the aircraft computer. These electrical connection means can consist, as shown, of the lugs C which are inserted into tapped holes T (FIG. 16a) made in the axial rod 22 and in the proximal electrode 17.

The receptacle 12 includes a cylindrical body 23 in which the magnetic head is housed, and an end cap 24 comprising a flap valve 25 secured, for example, to the end cap 24 by crimping 26, which is normally closed but is capable of being opened by the action of the magnetic head when the magnetic head is completely inserted into the receptacle, a spring 27 being placed between the end cap 24 and the receptacle.

In reference to FIGS. 10 to 15, the detector is furthermore provided with attachment means for attaching the detection head inside the receptacle and locking means for locking the attachment means.

The attachment means for attaching the magnetic head inside the receptacle include twist-lock attachment means. To that end, the magnetic head comprises at least two radial pins 28 that engage with at least two corresponding L-shaped notches 29 made in the receptacle.

As for the locking means, they are formed by a lock ring 30 rotatably mounted on the magnetic head and which includes at least two bosses 31 which engage with the at least two corresponding notches 32 made in the receptacle and in the ring.

A spring 33 acts on the lock ring in order to hold the bosses 31 in the notches 32 in such a way as to prevent rotation of the magnetic head in relation to the receptacle.

Thus, in order to unlock the head and thereby avoid any inadvertent disconnection of the magnetic head, first the lock ring 30 needs to be moved away by pulling upward against the force exerted by the spring 33. The magnetic head can then be turned until it can be released from receptacle.

Such an arrangement also makes it possible to avoid any incorrect installation of the magnetic head in the receptacle, with the return of the lock ring by the action of the spring 33 making it possible to indicate to operators that the magnetic head is correctly installed in the receptacle.

In reference to FIGS. 16a and 16b in which the relatively light areas Z1 represent the conductive zones and in which the relatively dark zones Z2 are insulating zones, as indicated earlier, the magnetic head comprises two coaxial electrodes 17 and 18. These electrodes are made of electrically conductive material coated with an insulator. In particular, electrically conductive zones Z1 are made in front of the air gap zone.

For example, the electrodes are made of aluminium and are coated with an insulator layer formed by hard sulphuric acid anodizing treatment so as to form, for example, a layer of insulator coating with a thickness of between 30 and 50 microns, with certain zones of the electrodes being remachined afterward (or spared during the coating process) and then treated by alodine chemical conversion to ensure electrical conductivity.

Naturally, the scope of the invention will not be exceeded if the electrodes are made of another material or are coated with an insulator layer of another type.

For example, it is possible as a variant to coat the electrodes with a layer of insulating material and to make the electrically conductive zones by local machining, or to locally coat the electrodes with a layer of varnish before application of the insulating material, these layers of varnish subsequently being eliminated to leave bare the zones that are to be electrically conductive.

The electrically conductive zones Z1 of the electrodes are made in the air gap zone and in the electrical connection zone of the electrodes in the location of the attachment screws.

As shown in FIG. 16b, the air gap here consists of an insulating ring B, made of plastic material for example.

In the embodiment just described, the magnetic head includes two diametrically magnetized magnets placed with one as an extension of the other.

As a variant, as shown in FIGS. 17 to 20, it is also possible to equip the magnetic head with a single cylindrical magnet which furthermore constitutes one of the electrodes of the magnetic head.

In this case, the magnet, designated by reference number 35, is an electrically conductive magnet. For example, it is coated with a layer of nickel.

The second electrode 36 is formed by an added cylindrical part which surrounds the magnet and which includes a set of openings 37 bounded by an electrically conductive material. These openings include peripheral edges and in particular electrically conductive peripheral sides that are opposite each other.

In this embodiment, the second electrode 36 can be held on the magnetic head by means of a seal 39.

In this way, only the magnet, which is one of the electrodes, is secured by threaded fastener to the body of the magnetic head.

Although the embodiment described earlier in reference to FIGS. 3 to 15 is advantageous to the extent that the magnet is protected by a sleeve formed by the two electrodes, one placed as an extension of the other, this embodiment is advantageous to the extent that it allows a magnet with a greater volume to be used, thanks to the elimination of one of the electrodes.

In reference to FIG. 19, electrical continuity is obtained in the magnetic head by the centre screw that attaches the magnet, by the electrically conductive magnet itself, and, on the other side of the air gaps, by the second electrode 36, by an electrical continuity spring 40, and a cylindrical assembly part 41 placed between the magnet and the body of the magnetic head.

This electrical circuit is closed or, in any event, the resistance thereof is reduced when a metal particle is present in the air gap between the magnet and the second electrode, such that an electric current can flow from the conductive zone to the electrical wires of the magnetic head.

As indicated earlier, the magnet has a large volume in this embodiment. In addition, this embodiment has a simple architecture which is easy to assemble.

Furthermore, the second electrode 36 includes a plurality of air gaps 37, each of which located between the magnet and an opening 37, which increases the number of detection zones for detecting metal particles.

Although the magnetic head only includes a single element in the described embodiments, it is also possible as a variant to use a plurality of magnets.

Lastly, note that the second electrode 36 includes, as shown in FIG. 18, an electrically insulating annular edge 42 in its end area, partially covering the end of the magnet in such a way that, in the absence of the removable electrode 36, such as by omission during reassembly, an electrical continuity arises between the magnet and the receptacle, indicating an assembly error.

In the second embodiment described earlier in reference to FIGS. 17 to 22, the magnetic head includes two electrodes, one consisting of the magnet and the other consisting of an added electrode 36 installed on the body of the magnetic head by means of a holding part, in the present case seal 39.

In another embodiment shown in FIGS. 20 to 23, in which one can recognize the magnetic head 11 provided with its axial body 14 having a generally cylindrical shape and equipped with twist-lock attachment means and the lock ring 30, and in which one can also recognize the diametrically magnetized magnet 35 constituting one of the electrodes of the magnetic head, in this embodiment the second electrode is formed inside the receptacle 12.

Here, the end cap 24 of the receptacle, which is installed so as to slide in relation to the body 14 with the placement of a spring 27 in between, is provided with a set of openings, such as 45, the longitudinal edges of which are electrically conductive, for example by machining performed after the deposition of an insulating coating.

This embodiment is advantageous to the extent that the second electrode is replaced with the end cap 24 of the receptacle and thus makes it possible to increase the volume of the magnet.

As shown in FIG. 23, in this embodiment the path of electrical continuity on the one hand passes axially through the body of the receptacle and along the conductive coating of the magnet, and, on the other hand, along the cap 24, the cylindrical assembly part 40, and then to an internal lug 46.

This circuit of electrical continuity is closed or the electrical resistance thereof decreases when a particle P of metal is located between the magnet and the end cap of the magnetic head.

As in the embodiment described earlier, this embodiment makes it possible to increase the diameter of the magnet and consequently the volume thereof.

The essential parts of the magnetic head have a cylindrical shape, which makes for easier cleaning of the particles during maintenance operations so that they can be analysed.

This embodiment also has a plurality of air gaps, which increases the number of detection zones.

In this embodiment, the magnetic head includes a single magnet. As a variant, it is also possible to use two welded cylindrical magnets to concentrate the particles.

FIGS. 25 to 31 show a fourth embodiment of a magnetic head and of a magnetic detector.

This embodiment differs from the embodiment described earlier in reference to FIGS. 20 to 24 in that the magnetic head comprises a plurality of diametrically magnetized magnets.

The electrodes, such as 48 and 49, are distributed angularly about the magnets with an insulating coating placed in between, for example by overmoulding with an elastomer, plastic, or resin, said overmoulding extending, on the one hand, between the electrodes and the magnets, and, on the one hand, between the electrodes.

Each of the electrodes 48 and 49 is made of a single part which includes, with regard to the electrode 48 and the electrode 49, a base 55 from which a set of teeth 51 extends. As shown in FIGS. 29 and 30, the electrode 48 is installed coaxially in the other electrode 49 in such a way that the each of the teeth of one of the electrodes fits between two teeth of the other electrode and the assembly is subsequently overmoulded.

In this embodiment, as shown in FIG. 31, the circuit of electrical continuity is closed when a magnetic particle P lies between two consecutive electrodes 48 and 49.

As described earlier, each electrode is made, for example, of aluminium coated with a coating serving as protection against corrosion and providing electrical insulation. This may consist, for example, of hard sulphuric acid anodizing. Certain parts of the electrodes are machined to eliminate the coating and expose the bare aluminium. The various components are assembled. Overmoulding with an elastomer is then performed.

Naturally, the scope of the invention is not exceeded if other processes, such as resin coating, are used. Machining can then be performed for local removal of the insulating coating in order to obtain an electrically conductive zone on each electrode.

In the various embodiments which have been described, the magnets are advantageously Neodymium magnets. The use of Neodymium Iron Boron grades, such as 45SH, which afford a high level of power while withstanding high temperatures on the order of 150° C., for example, may be considered.

The invention claimed is:

1. A magnetic head for a magnetic detector for detecting metal particles in a hydraulic circuit comprising an axial body internally comprising at least two magnets, at least two electrodes, each defining an air gap zone located in the magnetic field created by the magnet, such that the circuit creates a particle alignment zone in the air gap, and means for electrically connecting the at least two electrodes, wherein the at least two magnets are diametrically magnetized magnets arranged axially, a first magnet of the at least two magnets as an extension of a second magnet of the at least two magnets, and spaced apart from each other so that the pole of the first magnet is located in front of an opposite pole of the second magnet, and the at least two electrodes are arranged around the at least two magnets respectively.

2. The magnetic head according to claim 1, wherein at least one of the at least two electrodes is secured to the body by threaded fastener.

3. The magnetic head according to claim 1, wherein the at least two electrodes each include a set of openings comprising two electrically conductive zones that are opposite each other and each electrode of the at least two electrodes defining an air gap.

4. The magnetic head according to claim 3, wherein the magnet is electrically conductive and constitutes one electrode of the at least two electrodes of the magnetic head.

5. The magnetic head according to claim 1, wherein each electrode of the at least two electrodes includes a set of teeth extending axially from a base, the at least two electrodes being placed coaxially one inside the other around the at least two magnets in such a way that the teeth of a first electrode of the at least two electrodes are placed between the teeth of a second electrode of the at least two electrodes with an insulator placed in between.

6. The magnetic head according to claim 1, wherein each electrode of the at least two electrodes is made of an electrically conductive material coated with an insulating material, and including electrically conductive zones without insulation in the location of the air gap zone, and means for electrically connecting the at least two electrodes.

7. The magnetic head according to claim 5, wherein the insulator is provided by over-moulding with an insulating material.

8. The magnetic head according to claim 1, comprising means for attaching the magnetic head to a receptacle and means for locking the attachment means.

9. The magnetic head according to claim 8, wherein the attachment means comprise twist-lock attachment means, the locking means comprising a lock ring capable of preventing a rotation of the twist-lock attachment means.

10. A magnetic head according to claim 1, wherein the at least two magnets are permanent magnets made of Neodymium.

11. A magnetic metal particle detector in a hydraulic circuit, said detector comprising a magnetic head according to claim 1 and a receptacle in which the magnetic head is placed.

12. The magnetic detector according to claim 11, wherein the receptacle comprises an end cap in which the at least two magnets are housed.

13. The magnetic detector according to claim 12, wherein the end cap of the receptacle constitutes one of the electrodes of the at least two electrodes of the magnetic detector and includes a set of openings each of which defining an air gap, each opening comprising two electrically conductive zones that are opposite each other.

14. The magnetic detector according to claim 12, wherein the end cap includes a flap drawn to the closed state and which can be actuated to the open state by the action of the magnetic head.

\* \* \* \* \*